US012593964B2

(12) United States Patent
    Pollock

(10) Patent No.:     US 12,593,964 B2
(45) Date of Patent:         Apr. 7, 2026

(54) ENDOSCOPE OVERCOVERS FOR WHEELS AND HANDLES

(71) Applicant: Boston Scientific Scimed, Inc., Maple Grove, MN (US)

(72) Inventor: Ryan Vincent William Pollock, Sterling, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 589 days.

(21) Appl. No.: 18/053,849

(22) Filed: Nov. 9, 2022

(65) Prior Publication Data

US 2023/0147343 A1     May 11, 2023

Related U.S. Application Data

(60) Provisional application No. 63/277,803, filed on Nov. 10, 2021.

(51) Int. Cl.
    _A61B 1/00_         (2006.01)
    _A61B 1/005_        (2006.01)
    _A61B 17/00_           (2006.01)

(52) U.S. Cl.
    CPC ........ _A61B 1/0052_ (2013.01); _A61B 1/00042_ (2022.02); _A61B 1/00121_ (2013.01); _A61B 2017/00424_ (2013.01)

(58) Field of Classification Search
    CPC .............. A61B 1/0052; A61B 1/00121; A61B 1/00142; A61B 1/00042; A61B 1/00066; A61B 1/00068; A61B 1/00131; A61B 1/00147; A61B 1/0014; A61B 2017/00424; A61B 2017/00429; B25G 1/102
    See application file for complete search history.

(56) References Cited

U.S. PATENT DOCUMENTS

| | | | |
|---|---|---|---|
| 5,363,843 A | | 11/1994 | Daneshvar |
| 5,507,717 A | * | 4/1996 | Kura .................... A61B 1/0052 |
| | | | 600/146 |
| 5,562,602 A | | 10/1996 | Yabe et al. |
| 5,674,180 A | | 10/1997 | Yabe et al. |
| 5,695,449 A | | 12/1997 | Moriyama |
| 9,204,876 B2 | | 12/2015 | Cappola et al. |
| 10,588,495 B2 | | 3/2020 | Simmons et al. |
| 2008/0119696 A1 | * | 5/2008 | Moriyama ........... A61B 1/0052 |
| | | | 600/146 |
| 2019/0320881 A1 | * | 10/2019 | Grossman .......... A61B 1/00121 |
| 2020/0323418 A1 | | 10/2020 | Narayana et al. |
| 2021/0393115 A1 | * | 12/2021 | Sciortino ........... A61B 1/00042 |
| 2023/0309790 A1 | * | 10/2023 | Poulose ............... A61B 1/0014 |
| | | | 600/146 |

OTHER PUBLICATIONS

International Search Report and Written Opinion in International Application No. PCT/US2022/079524, mailed Feb. 9, 2023 (11 pages).

* cited by examiner

_Primary Examiner_ — Michael J Carey
_Assistant Examiner_ — Olivia Grace Starkey
(74) _Attorney, Agent, or Firm_ — Bookoff McAndrews, PLLC

(57)         ABSTRACT

A medical device including a handle and a flexible member controlled by the handle, the handle including one or more knobs, each of the one or more knobs having a plurality of protrusions spaced circumferentially from one another, wherein the medical device comprises one or more grip-enhancing features configured to be removably coupled to the one or more knobs.

8 Claims, 9 Drawing Sheets

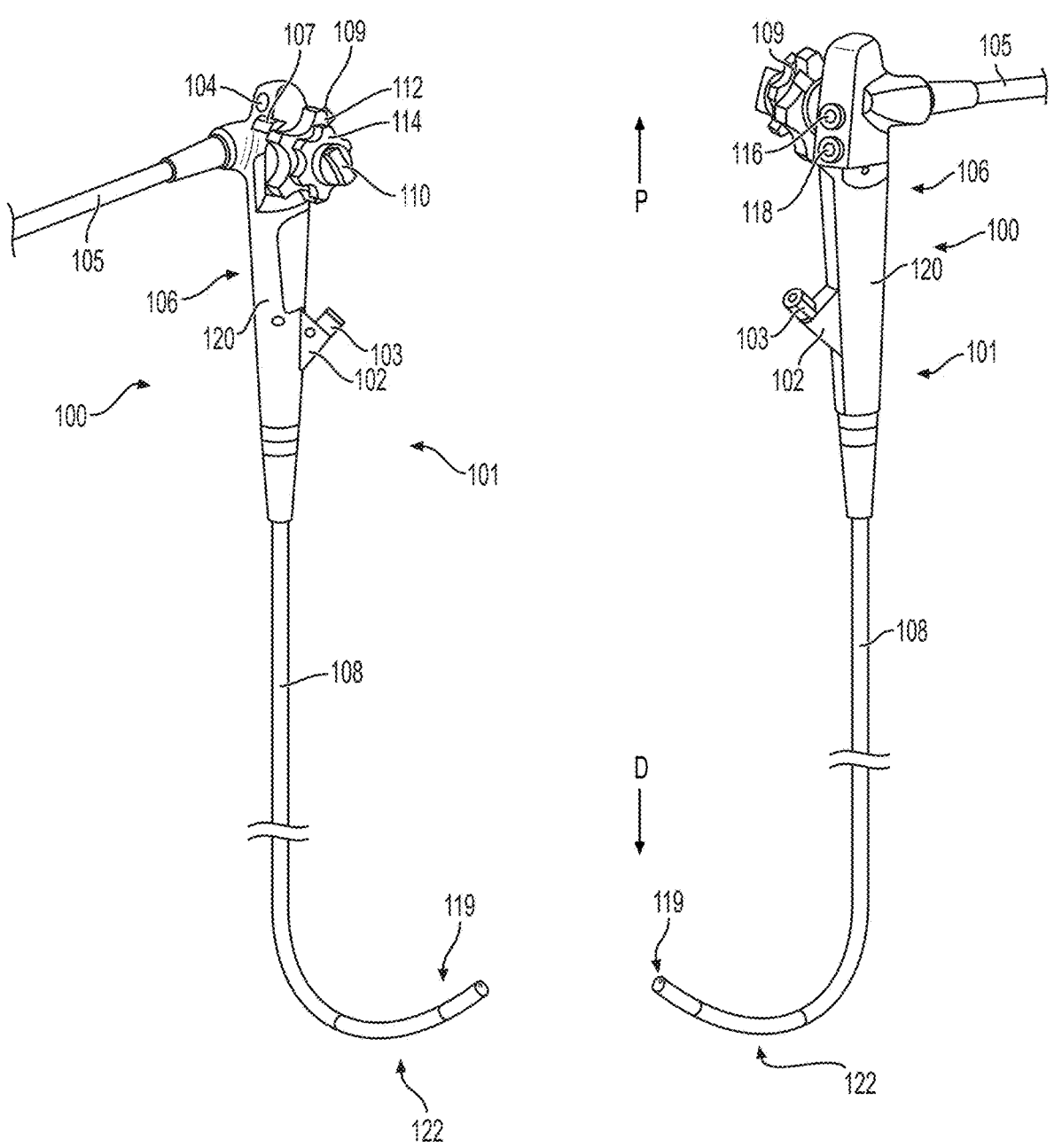
FIG. 1A          FIG. 1B

ENDOSCOPE OVERCOVERS FOR WHEELS AND HANDLES

CROSS-REFERENCE TO RELATED APPLICATIONS

This application claims the benefit of priority from U.S. Provisional Application No. 63/277,803, filed on Nov. 10, 2021, which is incorporated by reference herein in its entirety.

TECHNICAL FIELD

This disclosure relates generally to medical device accessories and extensions. More specifically, embodiments of the present disclosure relate to add-on overcovers for control knobs and handle of an endoscope or other medical device.

BACKGROUND

Endoscopes, in particular control knobs and the handle of an endoscope, have been harmonized to a similar design and size. For example, single use endoscopes attempt to mimic the human interface dimensions as closely to the reusable endoscopes as possible. Endoscope sizes have not been optimized to the variance in hand sizes of endoscope operators globally. Due to training and experience, there is significant resistance to change in the design of endoscopes to better suit the population or offer adjustability to the endoscope itself to fit the endoscope operator's hands. As a result, endoscope operators often use two hands to operate the control knobs or contort their hands into unusual shapes during a procedure. This further results in increased stress and muscle fatigue on the endoscope operator's hands during extended procedures or multiple procedures in a day or at a time.

SUMMARY OF THE DISCLOSURE

According to an example, a medical device may include a handle and a flexible member controlled by the handle, the handle including one or more knobs, each of the one or more knobs having a plurality of protrusions spaced circumferentially from one another, wherein the medical device may comprise one or more grip-enhancing features configured to be removably coupled to the one or more knobs.

In another example, the one or more grip-enhancing features may include a first grip-enhancing feature and a second grip enhancing feature configured to be removably coupled to a same knob of the one or more knobs. At least one of the grip-enhancing features may be configured to at least partially cover each of the plurality of protrusions of a given knob of the one or more knobs. At least one of the grip-enhancing features may be configured to at least partially cover, at most, less than an entirety of the plurality of protrusions of a given knob of the one or more knobs. The first grip-enhancing feature may include a plurality of protrusions and the second grip-enhancing feature may include a plurality of protrusions, wherein the plurality of protrusions of the first grip-enhancing feature may have a first extension length from a center of the first grip-enhancing feature, wherein the plurality of protrusions of the second grip-enhancing feature may have a second extension length from a center of the second grip-enhancing feature, wherein the first extension length and the second extension length may be different. At least one of the grip enhancing features may include a resilient overcover that is movable from a resting configuration to an expanded configuration, wherein the resilient overcover may be biased to the resting configuration. At least one grip-enhancing feature may have alternating protrusions and recesses spaced circumferentially from one another, wherein a number of the alternating protrusions may equal a number of the protrusions on a given knob of the one or more knobs. At least one grip-enhancing feature may be generally ring-shaped and includes a central opening, wherein each of the alternating protrusions may be positioned radially outward of the central opening. A grip-enhancing feature may include an outer surface comprising a tacky material. At least one grip-enhancing feature may comprise one or more tabs configured to snap onto a respective protrusion of the plurality of protrusions. Each of the one or more tabs may comprise a side wall extending along a first axis, a ridge extending radially inward from an end of the side wall, a rim extending radially inward from an end of the ridge, and a recess extending along an interior of the ridge between the side wall and the rim. Each tab may be configured to flex with respect to a remainder of the grip-enhancing feature about a joint. An additional grip-enhancing feature may be configured to be removably coupled to the handle, the additional grip-enhancing feature may include a slit configured to enable the grip-enhancing feature to open and close around the handle and a grip portion, wherein the grip portion may include an undulating pattern to match contours of the underlying handle. An outer surface of the additional grip-enhancing feature may include a tacky material. At least one grip-enhancing feature may be configured to be removably coupled directly to exactly one of the plurality of protrusions of the one or more knobs.

According to an example, a kit may comprise a plurality of grip-enhancing features for a handle of an endoscope, wherein the plurality of grip-enhancing features may include a first grip-enhancing feature and a second grip-enhancing feature, wherein the first grip-enhancing feature and the second grip-enhancing feature may be configured to be coupled to a same knob of the endoscope to provide different grip sensations to the same knob. The different grip sensations may include different spacing between adjacent finger protrusions, different tackiness, different thicknesses or lengths or widths of protrusions of the respective grip-enhancing features, and/or different patterned surfaces on outer surfaces of the respective grip-enhancing features. An additional grip-enhancing feature may be configured to be removably coupled to the handle, the additional grip-enhancing feature may include a slit configured to enable the grip-enhancing feature to open and close around the handle and a grip portion, wherein the grip portion may include an undulating pattern to match contours of the underlying handle.

According to an example, an overcover for one or more endoscope knobs may include a ring-shaped center including an opening extending therethrough, at least three protrusions positioned radially outward of the ring-shaped center, and circumferentially spaced from one another, each of the at least three protrusions defining a hollow interior, wherein the hollow interior of each of the at least three protrusions opens into the opening of the ring-shaped center. An entirety of the overcover may be formed of a resilient material.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 1A and 1B are perspective views of an exemplary endoscope, according to aspects of this disclosure.

DETAILED DESCRIPTION

Figure 2A:
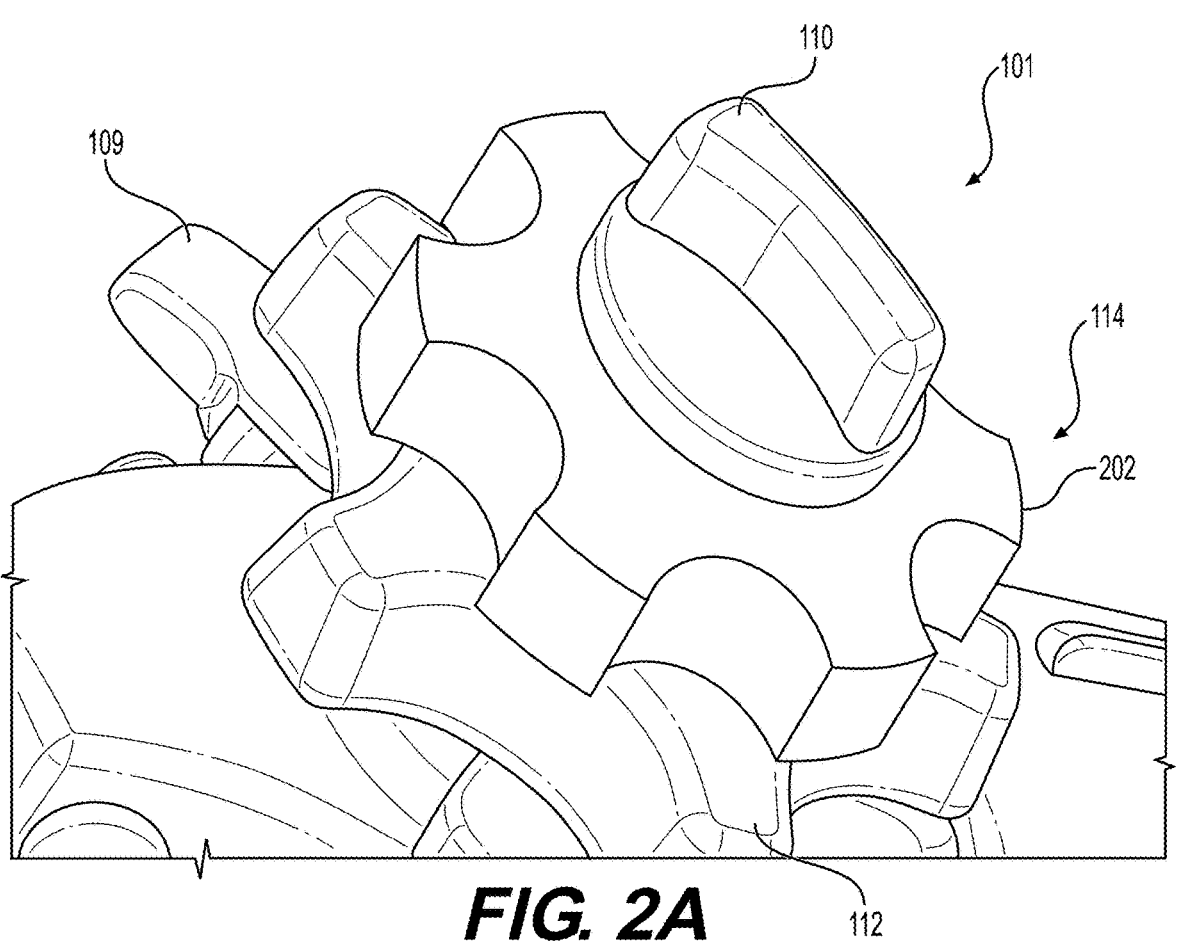
FIG. 2A is a perspective view of an endoscope knob with an exemplary overcover.

Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. Throughout the figures included in this application, arrows labeled "P" and "D" are used to show the proximal and distal directions in the figure. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Further, relative terms such as, for example, "about," "substantially," "approximately," etc., are used to indicate a possible variation of ±10% in a stated numeric value or range.

External, inexpensive, and customizable devices may help endoscope operators with both smaller and larger hand sizes to employ the functions of an endoscope with increased efficiency and reduce stress upon the endoscope operator. At least some examples of the present disclosure relate to add-on overcovers for control knobs and handle of an endoscope. Such devices may allow endoscope operators to select effective sizes, textures, and grip feel for control knobs and/or handles of an endoscope to fit their needs and reduce the stress incurred during a procedure.

FIGS. 1A and 1B show perspective views of an exemplary endoscope system 100. Endoscope system 100 may include an endoscope 101. Endoscope 101 may include a handle assembly 106 and a flexible tubular shaft 108. The handle assembly 106 may include a biopsy port 102, a biopsy cap 103, an image capture button 104, an elevator actuator 107, a first locking lever 109, a second locking lever 110, a first control knob 112, a second control knob 114, a suction button 116, an air/water button 118, a handle body 120, and an umbilicus 105. Any of the actuators, elevators, knobs, levers, ports, or caps of endoscope system 100 may serve any purpose and are not limited by any particular use that may be implied by the respective naming of each component used herein. The umbilicus 105 may extend from handle body 120 to auxiliary devices, such as a control unit, water supply, or vacuum source. Shaft 108 may terminate at a distal tip 119. Shaft 108 may include an articulation section 122 for deflecting distal tip 119 in up, down, left, and/or right directions. Handle body 120 may be tapered and may narrow as the handle extends distally such that the profile of the handle body 120 is smaller at its distal end than at its proximal end.

Although the term endoscope may be used herein, it will be appreciated that other devices, including, but not limited to, duodenoscopes, colonoscopes, ureteroscopes, bronchoscopes, laparoscopes, sheaths, catheters, or any other suitable delivery device or medical device may be used in connection with the devices of this disclosure.

FIG. 2A depicts a portion of endoscope 101 that includes first locking lever 109, second locking lever 110, first control knob 112, and second control knob 114. It will be appreciated that second control knob 114 has a greater diameter than second locking lever 110, and first control knob 112 has a greater diameter than second control knob 114. Second control knob 114 is coupled to a removable overcover 202. For example, overcover 202 may be removed from second control knob 114 and added onto first control knob 112. Overcover 202 may have a slightly smaller diameter than second control knob 114 (e.g., 20% less, 10% less, 5% less) so that it may tightly wrap around second control knob 114 or first control knob 112. It will be appreciated that more than one of overcover 202 may be used with endoscope 101. For example, each of the first control knob 112 and the second control knob 114 may be coupled to an overcover 202, or both the first control knob 112 and the second control knob 114 may be coupled to an overcover 202. In some examples, overcover 202 may be made of a soft pliable, elastic, and/or resilient material so that overcover 202 may stretch and/or compress as needed. For example, overcover 202 may stretch and/or compress around a substantial portion, a substantial entirety, or the entire outer surface of first control knob 112. For example, overcover 202 may stretch and/or compress around a substantial portion, a substantial entirety, or the entire outer surface of second control knob 114. For example, overcover 202 may stretch around second locking lever 110 to access first control knob 112 or second control knob 114.

In some examples, overcover 202 may be made of rubber type materials such as synthetic rubber, natural rubber, or polyurethanes. In some examples, overcover 202 may have different textures (e.g., bumpy, rough, smooth) that may enhance gripping capabilities. In some examples, overcover 202 may include sticky or tacky material on an outer surface and/or an inner surface. In some examples, sticky or tacky material may be a releasable adhesive, magnets, keyed features (i.e., components that fit within other slots or notches), hook and loop fasteners (e.g. VELCRO®), surface roughening, and/or additional material wrapped around inner and/or outer surface of overcover 202. Tacky material on outer and inner surfaces of overcover 202 may enhance gripping capabilities and/or improve adhesion of overcover 202 to first control knob 112 and/or second control knob 114.

Figure 2B:
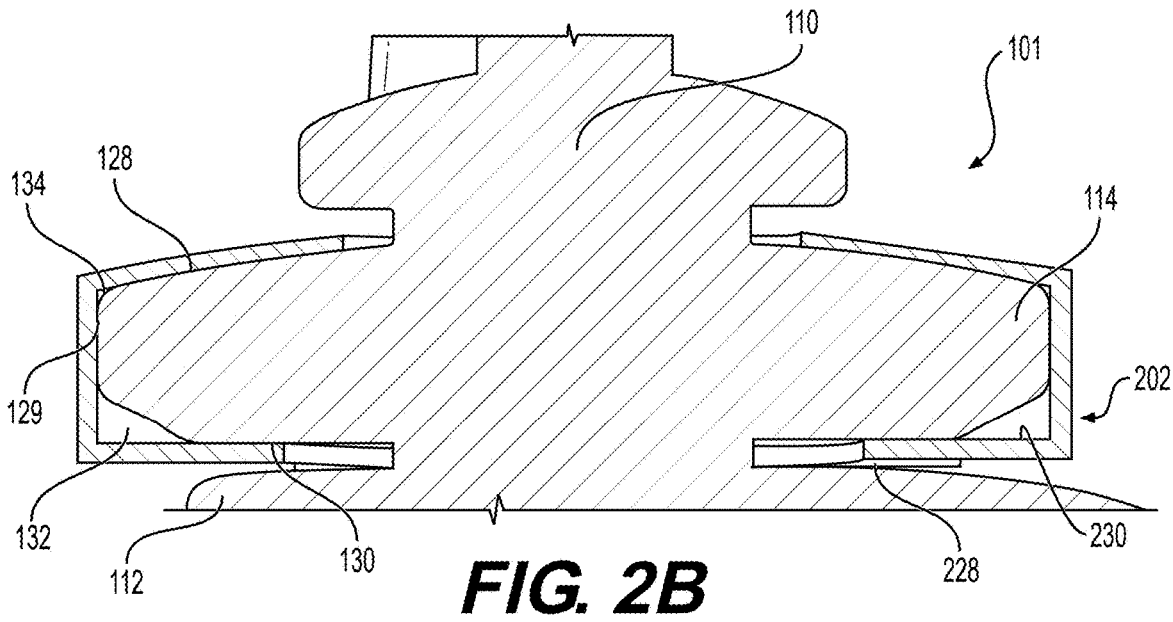
FIG. 2B is a cross sectional view of an endoscope knob with an exemplary overcover, according to aspects of this disclosure.

FIG. 2B is a cross sectional view of second locking lever 110, first control knob 112, and second control knob 114 of endoscope 101. Second control knob 114 is coupled to removable overcover 202. In one embodiment, an inner surface 230 of overcover 202 may contact and/or may be flush with at least a portion of the outer surface of second control knob 114, forming a gap 132 and/or a gap 134 between the outer surface of control knob 114 and inner surface 230 of overcover 202. For example, inner surface 230 of overcover 202 may contact a top face 128, a side face 129, and/or a bottom face 130 of second control knob 114. In one embodiment, the distance between an outer surface 228 and inner surface 230 of overcover 202 may vary. In one embodiment, gap 132 and gap 134 may be of varying sizes. In another embodiment, inner surface 230 may be flush with the entire outer surface of second control knob 114.

In another embodiment, overcover 202 may stretch around second locking lever 110 to access second control knob 114. Overcover 202 may then stretch around second control knob 114 so that inner surface 230 of overcover 202 may contact top face 128 and/or side face 129 of second control knob 114. Overcover 202 may then compress and/or revert towards its resting configuration so that inner surface 230 of overcover 202 may contact bottom face 130 of control knob 114, which holds overcover 202 in place during a procedure.

Figures 3A, 3B, 3C:
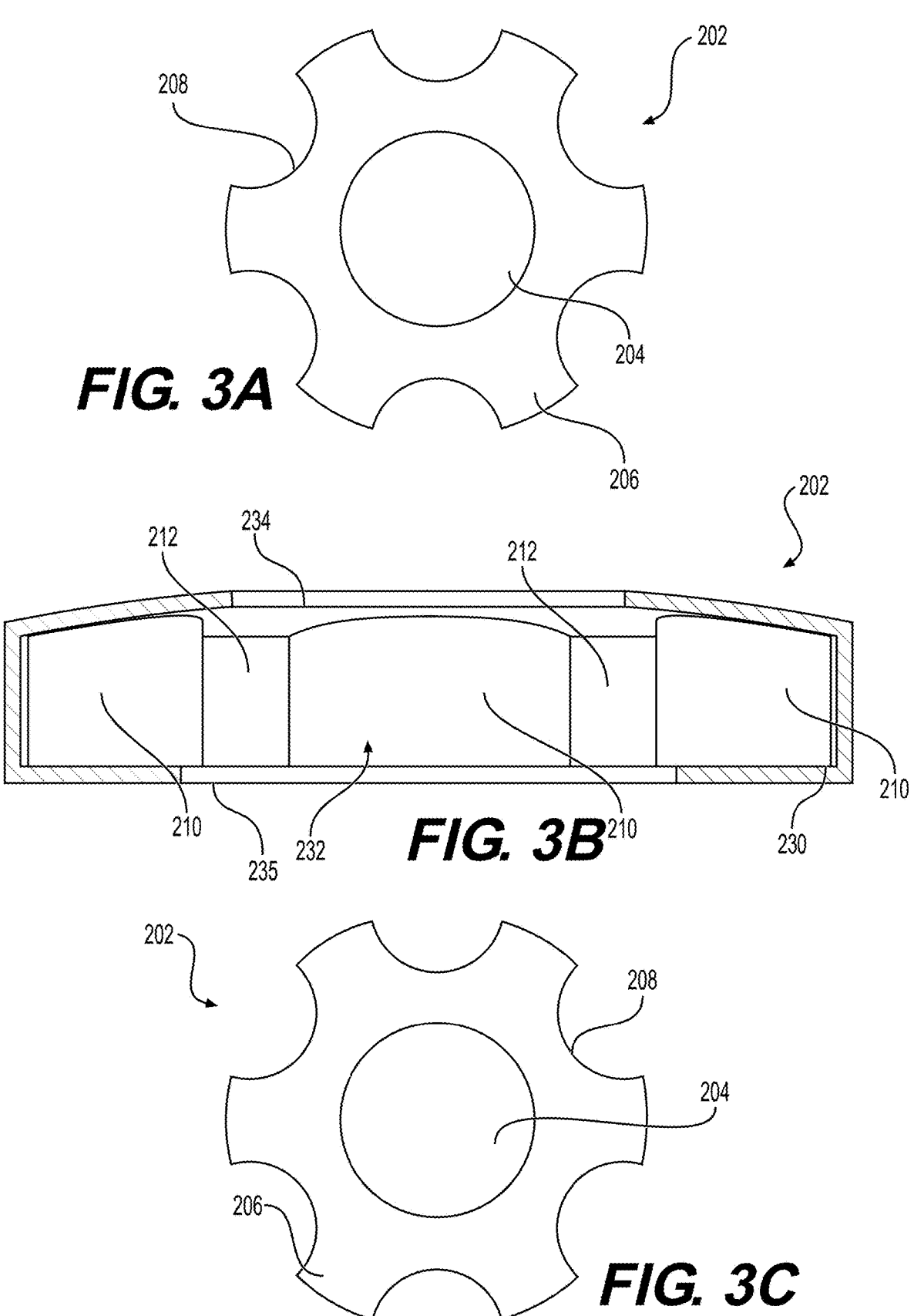
FIGS. 3A-3C are top, side cross sectional, and bottom views, respectively, of an exemplary overcover, according to aspects of this disclosure.

FIGS. 3A-3C show top, side cross sectional, and bottom views of overcover 202. Overcover 202 may be in a stretched configuration as described in FIGS. 2A-2B or a resting configuration. Overcover 202 may be materially biased to the resting configuration, which allows overcover 202 to stretch over second control knob 114 or first control knob 112, yet stay secure. As described above, overcover 202 may have a slightly smaller diameter than second control knob 114 (e.g., 20% less, 10% less, 5% less). In some examples, overcover 202 may include a central opening 204 on a top surface and a bottom surface. In some examples, opening 204 may be ring-shaped, although other suitable shapes also are contemplated. In some examples, the structure of overcover 202 may include alternating radial protrusions 206 and arched recesses 208 spaced circumferentially from one another, and form a continuous outer circumferential surface. The overall structure of overcover 202 may be generally similar to the shape of the control knobs on an endoscope. An inner surface 210 of recesses 208, an inner surface 212 of protrusions 206, an inner top surface 234, and an inner bottom surface 235 form a pocket 232 at the interior of overcover 202. In one example, pocket 232 may allow for overcover 202 to stretch around second locking lever 110 without any interference. In another example, pocket 232 may allow for overcover 202 to stretch and/or wrap around first control knob 112 and/or second control knob 114, without any interference.

In one embodiment, inner surfaces 210 and 212 of overcover 202 may correspond to the outer surface of first control knob 112 and/or second control knob 114, while outer surfaces of overcover 202 may have other shapes. For example, outer surfaces of overcover 202 may be straight/squared off recesses instead of arched recesses.

It will be appreciated that overcover 202 may come in different sizes (e.g., small, medium, and large). In some examples, small, medium, and large sizes may correspond to specific thicknesses, widths, lengths, and/or shapes of overcover 202 so that an endoscope operator may customize the control knobs to their preference. For example, one overcover 202 and a second overcover 202 may have protrusions 206 of varying lengths from a center of opening 204.

Figures 4A, 4B:
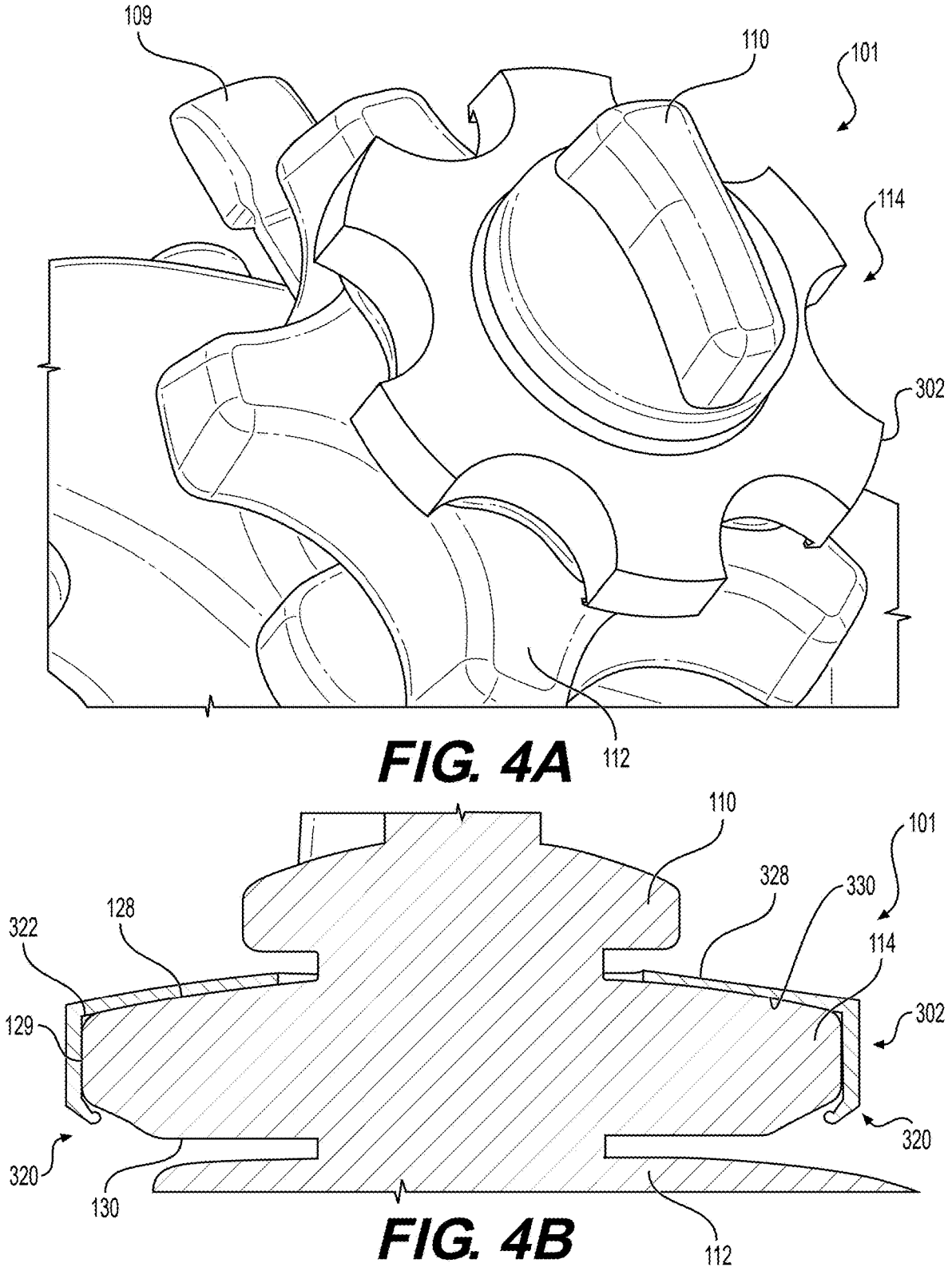
FIG. 4A is a perspective view of an endoscope knob with an exemplary overcover.
FIG. 4B is a cross sectional view of an endoscope knob with an exemplary overcover, according to aspects of this disclosure.

FIG. 4A depicts a portion of endoscope 101 that includes first locking lever 109, second locking lever 110, first control knob 112, and second control knob 114 coupled to a removable overcover 302. Overcover 302 may substantially cover the top surface and side surface of second control knob 114. In some examples, the diameter of overcover 302 may be exactly equal to or greater than the diameter of second control knob 114. In some examples, overcover 302 may be made of a semi-rigid plastic so that overcover 302 may be "snapped" onto second control knob 114. Overcover 302 may be generally rigid, but is also able to flex enough so that overcover 302 may be placed onto second control knob 114. When flexed, overcover 302 is biased to a resting configuration.

FIG. 4B is a cross sectional view of second locking lever 110, first control knob 112, and second control knob 114. Second control knob 114 is coupled to removable overcover 302 of endoscope 101. In one embodiment, an inner surface 330 of overcover 302 may contact top face 128 and side face 129 of second control knob 114. Inner surface 330 may be flush with top face 128 and side face 129 of second control knob 114 forming a gap 322 between outer surface of control knob 114 and inner surface 330 of overcover 302. In one embodiment, the distance between outer surface 328 and inner surface 330 of overcover 302 may vary. Overcover 302 may include a tab 320 that may deflect outward and "snap" into place once clearing any interference of second control knob 114. Tab 302 may contact the underside of fingers, indents, or the entire underside of second control knob 114.

Figure 5:
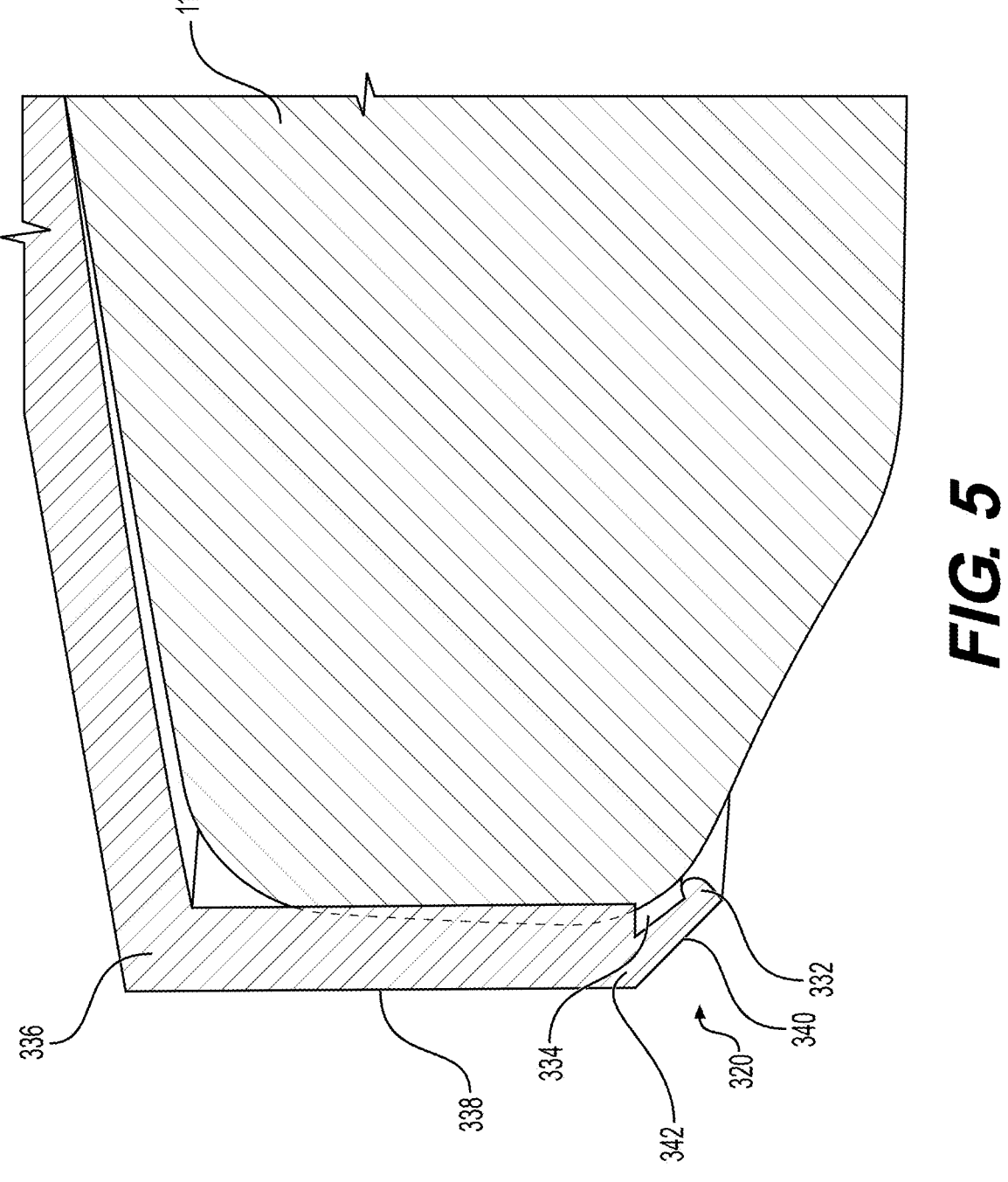
FIG. 5 is a cross sectional view of a portion of an endoscope knob with an exemplary overcover, according to aspects of this disclosure.

FIG. 5 provides a detailed view of second control knob 114 coupled to overcover 302 described in FIGS. 4A and 4B above. In one embodiment, overcover 302 may be moved in a circular motion around and/or up and down second control knob 114 until the structure of overcover 302 aligns with the fingers and indents of second control knob 114. Then, tab 320 may be flexed radially outward to allow a flexible joint 336 to be secured onto second control knob 114. As overcover 302 is pushed towards second control knob 114, a side wall 338 of overcover 302 and tab 320 may contact a side surface of a finger of second control knob 114. Side wall 338 and tab 320 are secured along the side surface of second control knob 114 until inner surface 330 is flush with top face 128 of second control knob 114. Joint 342 allows for tab 320 to move radially inward and "snap" into place with a rim 332 of tab 320 contacting an outside surface of second control knob 114. Tab 320 may include an inner circumferential recess 334 that forms a cavity between tab 320 and second control knob 114. Tab 320 may include a circumferential ridge 340 that is inclined radially inward from side 338. Rim 332 is a circumferential rim adjacent to recess 334 on ridge 340 and extends radially inward. Any interior surface of rim 332 may include tacky substances to improve adhesion to second control knob 114. For all embodiments, any given tab 320 may have different dimensions as any other tab 320. For example, a given tab 320 may be 1.5×, 2×, 3× the length of any other tab 320.

Figures 6A, 6B, 6C:
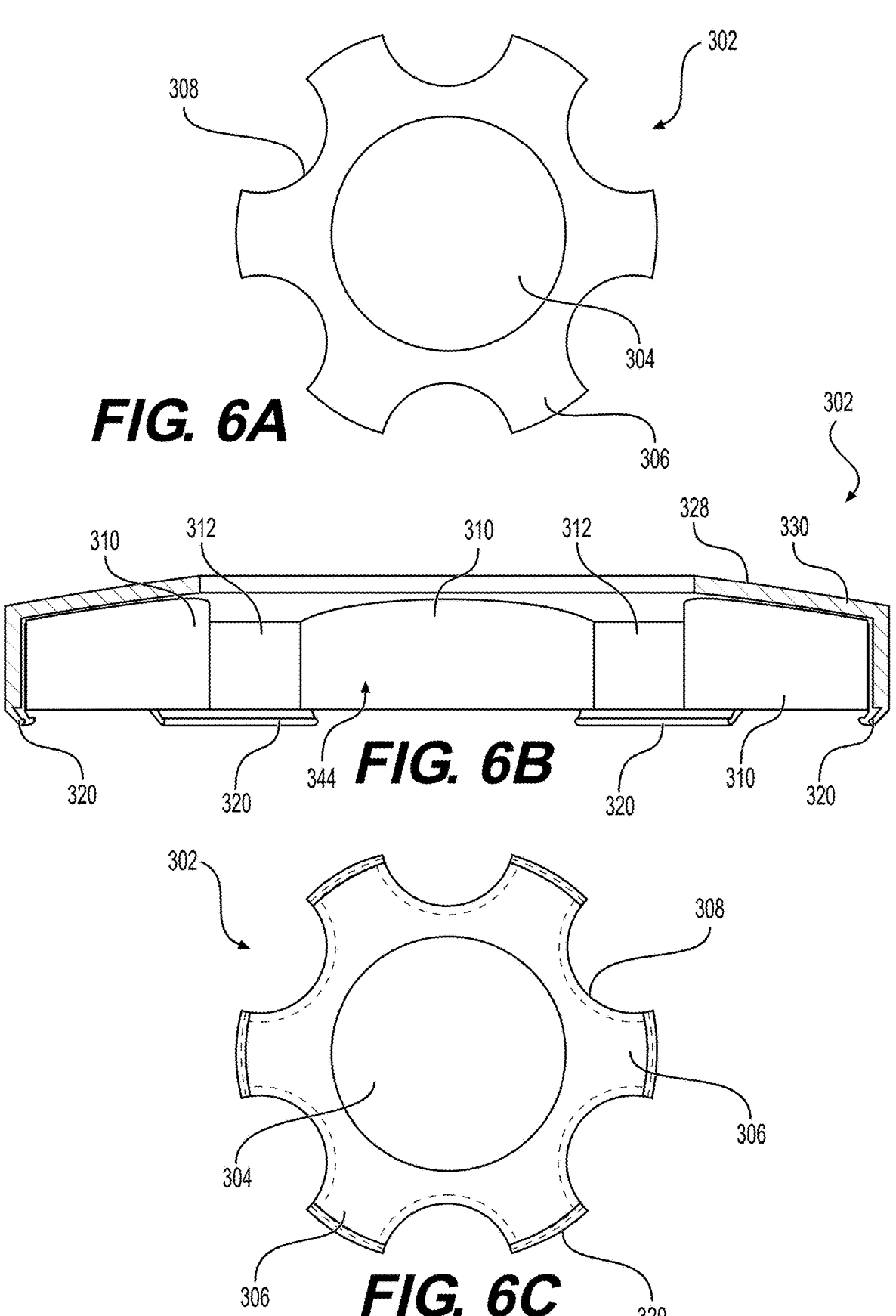
FIGS. 6A-6C are top, side cross sectional, and bottom views, respectively, of an exemplary overcover, according to aspects of this disclosure.

FIGS. 6A-6C show top, side cross sectional, and bottom views of overcover 302. In some examples, overcover 302 may include a central opening 304 on a top surface and a bottom surface. In one embodiment, opening 304 may be ring-shaped, although other suitable shapes also are contemplated. In one embodiment, the structure of overcover 302 may include alternating radial protrusions 306 and arched recesses 308 spaced circumferentially from one another, and form a continuous outer circumferential surface. An inner surface 310 of recesses 308 and an inner surface 312 of radial protrusions 306 define a hollow interior 344 that allows for overcover 302 to substantially cover the top surface and side surface of second control knob 114. Tab 320 may be found at the ends/bottoms of radial protrusions 306, at the ends/bottoms of recesses 308, and/or all around the bottom of overcover 302. It will be appreciated that the overcovers may come in different sizes (e.g., small, medium, and large). In some examples, small, medium, and large sizes may correspond to specific thicknesses, widths, lengths, and/or shapes of overcover 302 so that an endoscope operator may customize the control knobs to their preference.

Figure 7A:
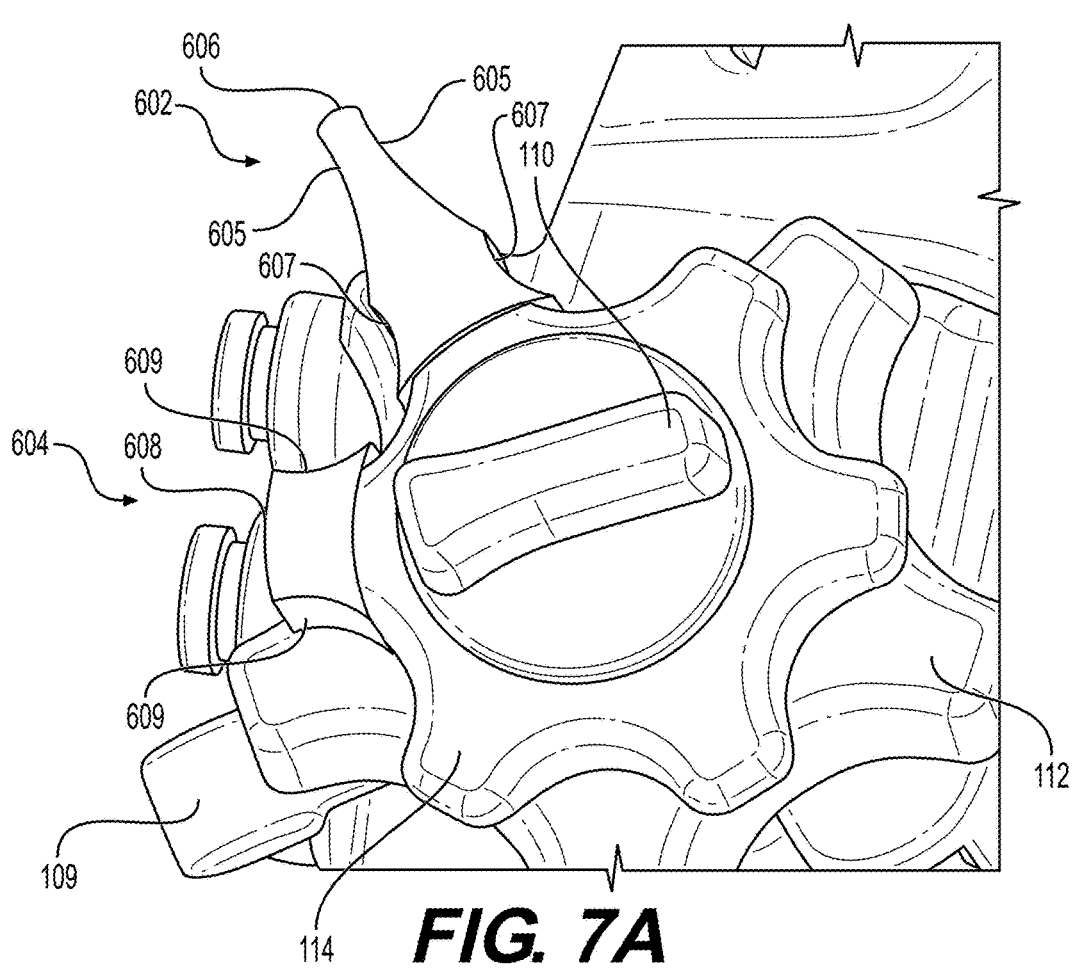
FIG. 7A is a perspective view of an endoscope knob with exemplary overcovers.

FIG. 7A depicts exemplary single finger overcovers 602 and 604. Single finger overcovers 602 and 604 may cover the fingers of second control knob 114 and/or first control knob 112. In some examples, single finger overcovers 602 and 604 may be made of an elastic material so that single finger overcovers 602 and 604 may stay attached to fingers of second control knob 114 and/or first control knob 112 based on elasticity (e.g., material reverting to a compressed configuration). In some examples, single finger overcovers 602 and 604 may stretch over a single finger of second control knob 114 and/or first control knob 112 with friction/tackiness being the primary resistance force of removal. Exemplary single finger overcover 602 may have opposing bottom grooves 607 that lead into concave extension areas 605 that meet at a tip 606 that may be pointed. The extension areas may be 2×, 3×, or 4× the length of control knob fingers from a radial central point. Exemplary single finger overcover 604 may have opposing bottom grooves 609 that meet at a tip 608 that may be flat. It will be appreciated that tips 606 and 608 of single finger overcovers 602 and 604, respectively, may take any shape and may be of different lengths. In some examples, single finger overcovers 602 and 604 may be combination overcovers (e.g., part of a set) that fit less than all fingers (e.g., exactly two, exactly three, exactly four, and exactly five).

Figure 7B:
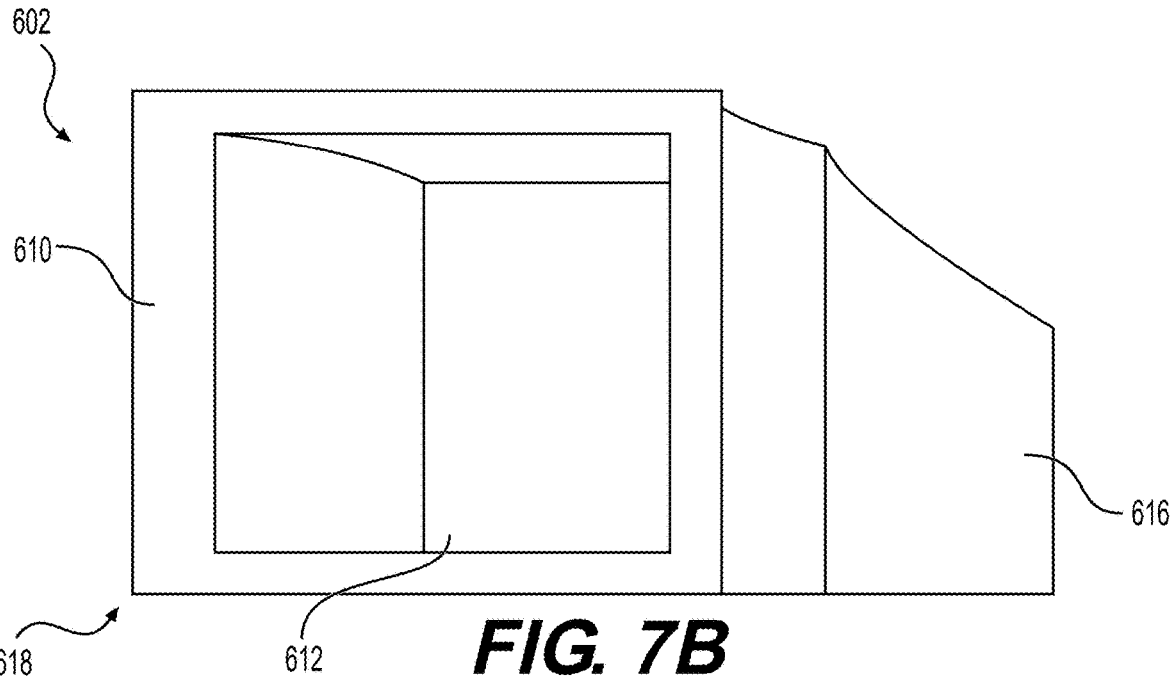
FIG. 7B is a side view of an exemplary overcover, according to aspects of this disclosure.

FIG. 7B is a side view of exemplary single finger overcover 602. Single finger overcover 602 may include a cavity 612 defined by one or more surfaces. In one embodiment, cavity 612 may have a generally square cross section starting at base 618, although other suitable cross sections also are contemplated. Cross section of cavity 612 may change depending on the body shape 616 of single finger overcover 602. It will be appreciated that body 616 of single finger overcover 602 may take any shape (e.g., cube, pyramid, irregular 3D shapes). Base 618 of single finger overcover 602 may include outer surface 610 that surrounds cavity 612. Outer surface 610 may be of varying thickness and may contact second control knob 114 and/or first control knob 112. It will be appreciated that multiple single finger overcovers 602 of varying shapes, sizes, textures, and designs may be attached to fingers of control knobs independently to customize the control knobs to the endoscope operator's preference. Single finger overcovers 602 may be of the same materials, grip, and tack as discussed above for exemplary overcovers.

Figures 8A, 8B:
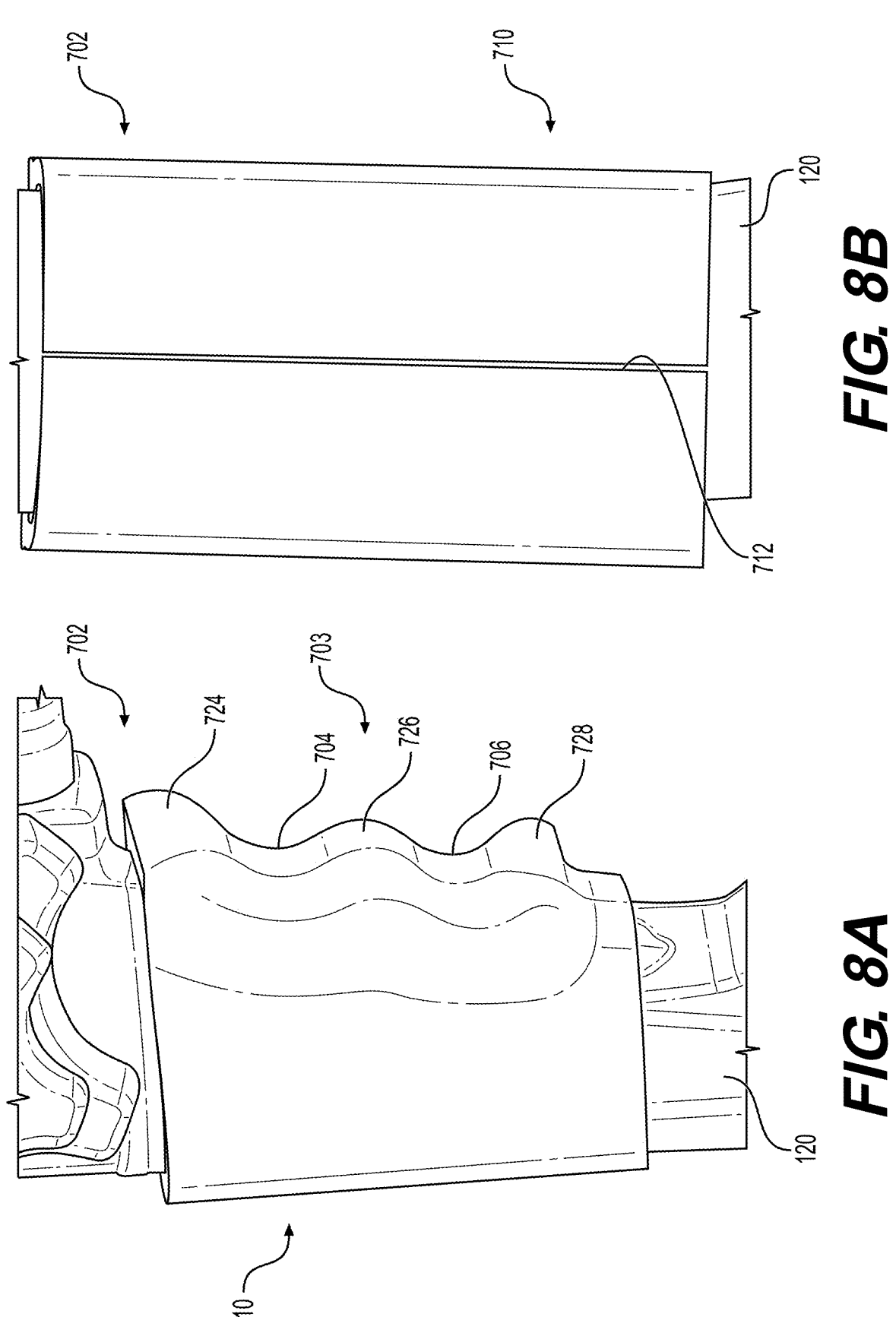
FIGS. 8A and 8B are perspective views of an endoscope handle with an exemplary overcover, according to aspects of this disclosure.

FIGS. 8A-8B depict a scope handle body 120 with a handle cover 702. The front (first side) of handle cover 702 may include an ergonomic grip 703. Ergonomic grip 703 may include a recess 704 between a bump 724 and a bump 726, and a recess 706 between a bump 726 and a bump 728. An endoscope operator may place fingers on recess 704 and recess 706 during an operation. Positioning of fingers may be further stabilized by bump 724, bump 726, and bump

728. In other words, ergonomic grip 703 may undulate to match the contours of the underlying handle cover 702. In some examples, ergonomic grip 703 may be made of rubber. A back 710 of handle cover 702 may be flat and may include a slit 712. Back 710 of handle cover 702 may be made of a semi-rigid elastic material which may allow the cover to open around the handle and "snap" together so that the inner surface of handle cover 702 is flush with the outer surface of scope handle body 120. In another embodiment, handle cover 702 may come in two pieces and snap together at one or more different junctions. For example, where slit 712 is shown.

Figures 9A, 9B:
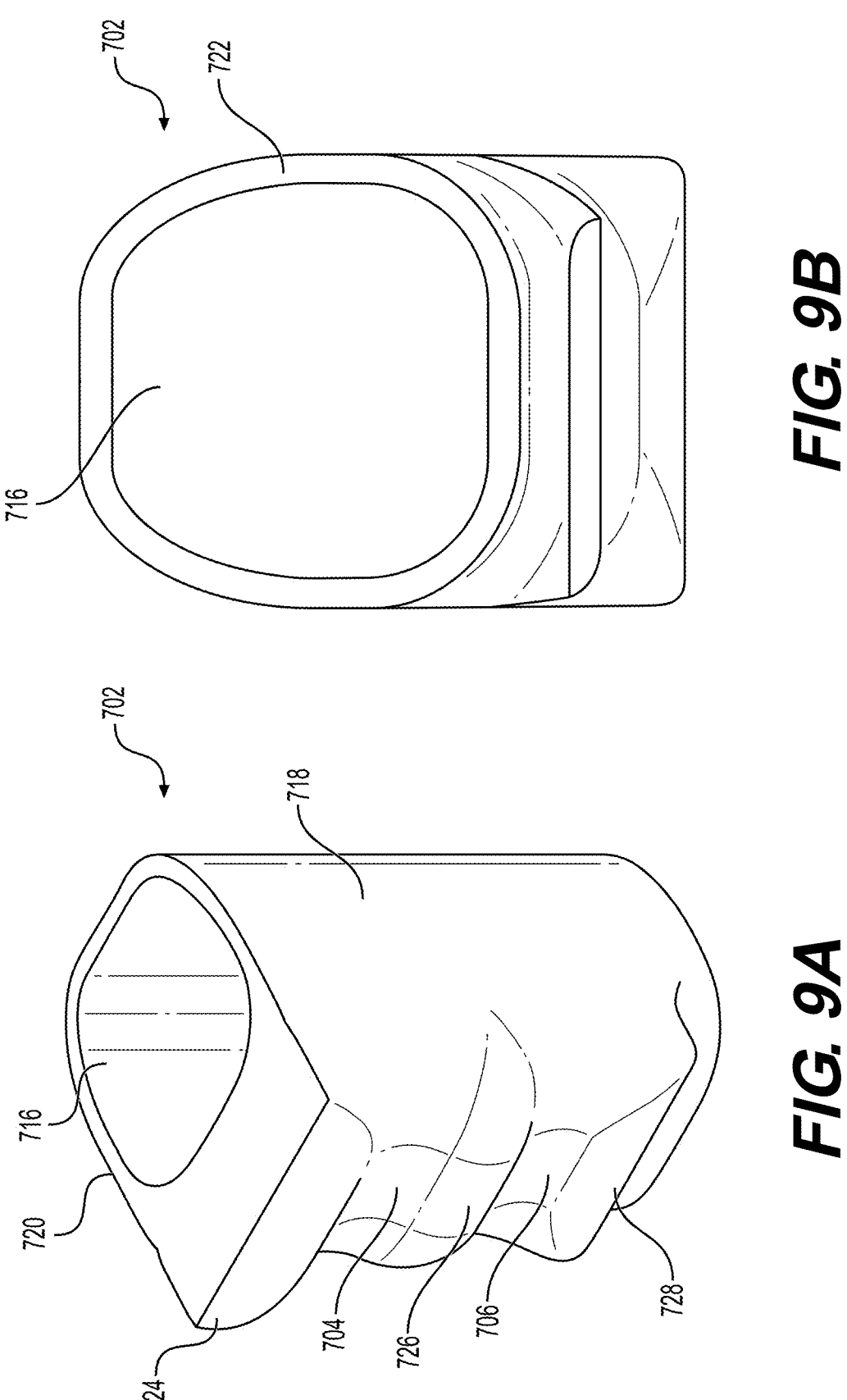
FIGS. 9A and 9B are perspective views of an exemplary handle overcover, according to aspects of this disclosure.

FIGS. 9A and 9B depict handle cover 702. Further to the features described above in FIGS. 8A-8B, handle cover 702 includes a channel 716 defined circumferentially by one or more surfaces. Channel 716 may have a generally circular cross-section. In one embodiment, channel may be wider at the proximal end of handle body 120 and more narrow at the distal end of handle body 120. In one embodiment, a surface 718 forming the body of channel 716 may be of varying widths so as to increase the diameter of handle cover 702 without changing the size of channel 716. This may help endoscope operator's with larger hands to use an endoscope with greater maneuverability. A top surface 720 of handle cover 702 and a bottom surface 722 of handle cover 702 may be of varying widths. It will be appreciated that handle cover 702 may come in different sizes (e.g., small, medium, and large). In some examples, small, medium, and large sizes may correspond to specific thicknesses, widths, lengths, and/or shapes of handle cover 702 so that an endoscope operator may customize the handle body of an endoscope to their preference. For example, an endoscope operator with larger hands may select a large sized handle cover 702 so as to increase the diameter of the handle body 120 of endoscope 101.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
a handle and a flexible member controlled by the handle, the handle including one or more knobs, each of the one or more knobs having a plurality of protrusions spaced circumferentially from one another; and
a grip-enhancing feature configured to be removably coupled to a knob of the one or more knobs,
wherein the grip-enhancing feature surrounds less than an entire perimeter of the knob, and wherein the grip-enhancing feature defines:
a first tip and a first opening, wherein the first opening is configured to receive a first protrusion of the plurality of protrusions;
opposing concave extension areas that meet at the first tip; and
opposing grooves disposed between the opposing concave extension areas and the first opening.

2. The medical device of claim 1, wherein the grip-enhancing feature is a first grip-enhancing feature, and wherein the medical device further comprises a second grip-enhancing feature, wherein the first grip-enhancing feature is configured to be removably coupled to a first protrusion of the plurality of protrusions of the knob of the one or more knobs, and wherein the second grip-enhancing feature is configured to be removably coupled to a second protrusion of the plurality of protrusions of the one or more knobs.

3. The medical device of claim 1, wherein the grip-enhancing feature includes a resilient overcover that is movable from a resting configuration to an expanded configuration, wherein the resilient overcover is biased to the resting configuration.

4. The medical device of claim 1, wherein the grip-enhancing feature includes an outer surface comprising a tacky material.

5. The medical device of claim 1, wherein the grip-enhancing feature is a first grip-enhancing feature, and wherein the medical device further comprises a second grip-enhancing feature configured to be removably coupled to the handle, the second grip-enhancing feature including:

a slit configured to enable the second grip-enhancing feature to open and close around the handle; and a grip portion, wherein the grip portion includes an undulating pattern to match contours of the handle.

6. The medical device of claim 5, wherein an outer surface of the second grip-enhancing feature includes a tacky material.

7. The medical device of claim 1, wherein the grip-enhancing feature is configured to be removably coupled directly to exactly one protrusion of the plurality of protrusions of the one or more knobs.

8. The medical device of claim 2, wherein the first grip-enhancing feature has a first length, wherein the second grip-enhancing feature has a second length, wherein the second length is less than the first length.

\* \* \* \* \*